(12) United States Patent
Klitgaard et al.

(10) Patent No.: US 6,379,339 B1
(45) Date of Patent: Apr. 30, 2002

(54) SYRINGE

(75) Inventors: Christian Peter Klitgaard, Smørum; Steffen Hansen, Hillerød, both of (DK)

(73) Assignee: Nova Nordisk A/S, Bagsvaerd (DK)

( * ) Notice: Subject to any disclaimer, the term of this patent is extended or adjusted under 35 U.S.C. 154(b) by 0 days.

(21) Appl. No.: 08/927,979

(22) Filed: Sep. 11, 1997

Related U.S. Application Data

(60) Provisional application No. 60/049,121, filed on Jun. 11, 1997.

(30) Foreign Application Priority Data

Sep. 13, 1996 (DK) .............................. 0990/96

(51) Int. Cl.[7] .......................... A61B 1/30; A61B 11/02; A61B 11/06
(52) U.S. Cl. .................................................. 604/207
(58) Field of Search ................... 604/187, 156, 604/207, 131, 232, 236, 181, 206–211, 117, 154–155; 128/DIG. 1, DIG. 2, 13; 206/364, 366, 365, 369

(56) References Cited

U.S. PATENT DOCUMENTS

| 286,605 A | * | 10/1883 | Grant | 604/226 |
|---|---|---|---|---|
| 1,272,742 A | * | 7/1918 | Weguelin et al. | 604/226 |
| 3,970,195 A | * | 7/1976 | Franklin | 206/380 |
| 4,863,433 A | | 9/1989 | Payne et al. | |
| 4,950,246 A | * | 8/1990 | Muller | 604/154 |
| 5,129,914 A | * | 7/1992 | Choi | 606/189 |

FOREIGN PATENT DOCUMENTS

| DE | 27 15 093 A1 | | 10/1977 | |
|---|---|---|---|---|
| EP | 0 279 583 | | 8/1988 | |
| EP | 0 697 222 A2 | | 2/1996 | |
| FR | 2648715 | * | 12/1990 | 604/226 |
| WO | WO 85/04590 | | 10/1985 | |

* cited by examiner

Primary Examiner—Manuel Mendez
(74) Attorney, Agent, or Firm—Skadden, Arps Slate Meagher & Flom LLP

(57) ABSTRACT

The present invention relates to syringes comprising a housing (1), a dose setting mechanism in the housing, an injection button (6), and a needle receiving member. By this syringe doses of a medicine can be set by the dose setting mechanism and by operating the injection button (6) the set dose can be pressed out from an ampoule accommodated in the housing (1) through a needle (5) mounted on the needle receiving member. The housing further comprises an accessible compartment covered by a lid (10) or a cap (8) in which compartment accessories (11) are stored.

8 Claims, 1 Drawing Sheet

SYRINGE

CROSS-REFERENCE TO RELATED APPLICATIONS

This application claims priority under 35 U.S.C. 119 of Danish application 0990/96 filed Sep. 13, 1996 and U.S. provisional application No. 60/049,121 filed Jun. 10, 1997, the contents of which are fully incorporated herein by reference.

BACKGROUND OF THE INVENTION

1. Field of the Invention

The invention relates to syringes of the kind comprising a housing, a dose setting mechanism in the housing, an injection button, and a needle receiving member, by which syringe doses of a medicine can be set by the dose setting mechanism and by operating the injection button can be pressed out through a needle mounted on the needle receiving member from an ampoule accommodated in the housing.

Such syringes are mainly developed to be used by patients, mainly diabetics, who have to frequently inject themselves with individually set doses of insulin. The syringes are often given a shape like a fountain pen so it may be carried by the patient all through the day and is always ready for an injection. The ampoule may contain medicine enough for several days, but the used needle must be removed after an injection and a new needle mounted before the next injection. This opens the need for extra needles which the patient further must bring with him. Also other kinds of equipment may be necessary so as strips by which the blood glucose concentration may be estimated and pills if the diabetic suffers from the type II diabetes which is treated partly by pills and partly by insulin injections. Consequently the syringe is mainly delivered in a small case which accommodates the syringe, a number of needles, possibly a ampoule with medicine etc. However, this already makes the patient less free than it was intended when the pen was developed as an device integrating all the most necessary parts. Especially the need for spare needles have to be met.

2. Description of the Related Art

EP 697 222 discloses fixing a tube containing a number of needles to a pen by a clip having oppositely directed C-shaped portions. This solution only transforms the inconvenience of having two parts to carry into the inconvenience of having a bulky thing to wear.

It is an object of the invention to provide a syringe by which this inconveniences are avoided.

SUMMARY OF THE INVENTION

The present invention is a syringe comprising a housing for containing an ampoule and having a needle receiving member; and a dose setting and injection mechanism in the housing for setting a desired dose of medicine and pressing the set dose of medicine out of an ampoule mounted in the housing. The housing has a compartment accessible by the user of such syringe for storing one or more accessories which are not normally mounted on the syringe when stored.

The compartment may according to the invention has a size enabling it to accommodate at least one needle stored in a needle magazine.

The compartment may according to the invention be a cavity in the housing covered by a lid, or it may be an inner space in a cap which is mounted on the housing or in a drawer which is slides into the housing.

BRIEF DESCRIPTION OF THE FIGURES

In the following the invention is further described with references to the drawing wherein.

DETAILED DESCRIPTION OF THE INVENTION

Figure 1:
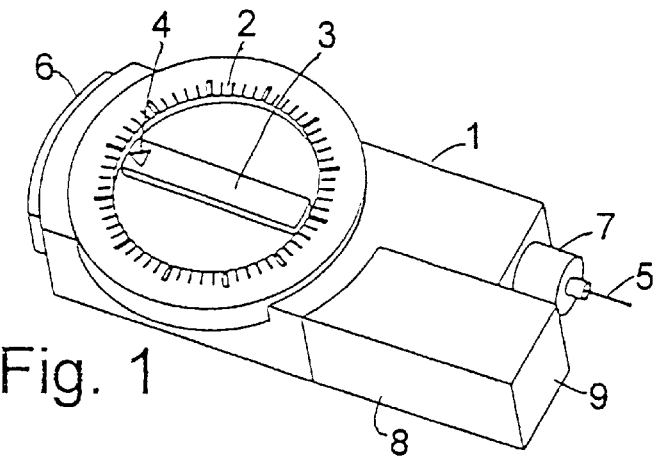
FIG. 1 shows a syringe with a compartment according to the invention, the compartment being closed by a cap.

FIG. 1 shows a preferred syringe having a compartment according to the invention. The syringe is of the type which due to the use of a flexible piston rod is shorter and broader than a conventional pen shaped syringe. Such syringes have a form lying between the size of a lighter and a pack of cigarettes and are consequently easy to carry in a pocket. Pen shaped syringes have through the time lost their slim design due to the fact that larger ampoules are used and the dose setting mechanism is extended by electronic displays which calls for a larger diameter of at least the proximal end of the pen. With such pen a compartment may be provided in the large diameter part of the syringe or in extensions of the pen, but such extensions will not surely make the pen more bulky. Consequently a new box shaped design as the one shown in FIG. 1 is preferred.

The syringe in FIG. 1 comprises a housing 1 carrying a scale 2 on which a dose may be set by rotating a finger grip 3 until an arrow 4 on this grip indicates the wanted dose on the scale 2. The dose may thereafter by pressing an injection button 6 be injected through a needle 5 which is carried in a needle hub 7 which is mounted on an needle receiving member on the syringe. A cap 8 covers a compartment in the housing.

Figure 2:
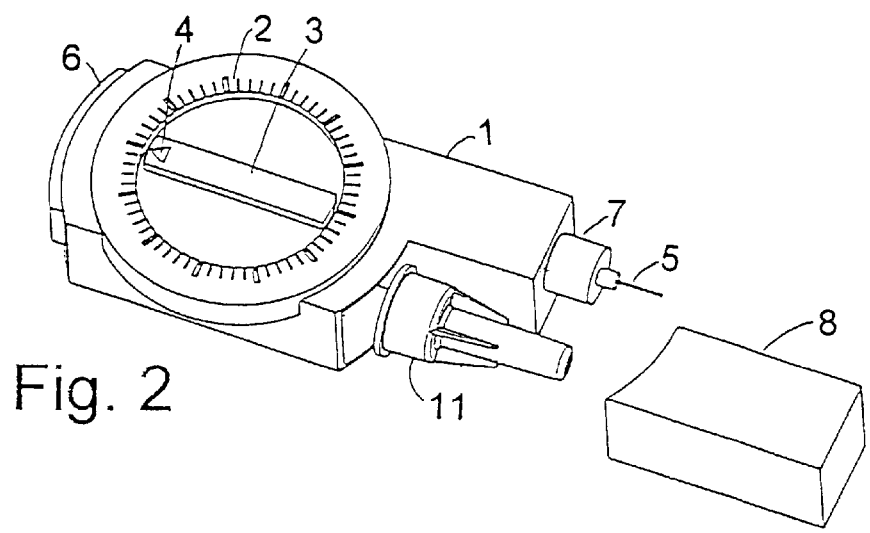
FIG. 2 shows the syringe in FIG. 1 with the cap off.

FIG. 2 shows the syringe of FIG. 1 with the cap 8 drawn off and a needle case 11 is sketched to show how such a needle case 11 which accommodates a needle as the needle 5 mounted in its needle hub 7 may be stored in the compartment. The cap is further so designed that its end surface 9 forms an abutment which may abut the skin during the injection.

Figure 3:
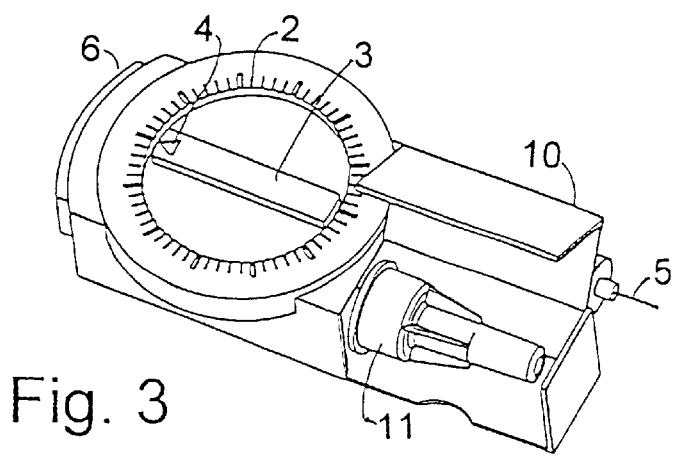
FIG. 3 shows another embodiment of a syringe with a compartment covered by a lid.

FIG. 3 shows a syringe corresponding to the one shown in FIGS. 1 and 2. In this syringe the compartment is totally integral with the housing and is accessible through a lid 10.

In the drawings the equipment in the compartment is shown as a needle, but many other kinds of accessories may be stored in the compartment, e.g. electronic devices which could ordinarily be integrated in a durable syringe but which are too expensive to discard with a disposable syringe. Such electronic devices may be different types of timers or devices for electronic reading of set doses or the number of doses left in the ampoule. Also things which the patient may want to have a hand so as instructions, swaps, tablets, aids for mounting or dismounting of the needle, etc.

What is claimed is:

1. A syringe comprising:

a housing having a space for containing an ampoule and having a needle receiving member;

a dose setting and injection mechanism in the housing for setting a desired dose of medicine and pressing the set dose of medicine out of an ampoule mounted in the housing; and wherein the housing has a compartment accessible by the user of such syringe for storing one or more accessories which are not normally mounted on the syringe when stored.

2. A syringe according to claim 1, wherein said compartment has a storage capacity large enough to accommodate at least one needle case.

3. A syringe according to claim 2, wherein the compartment is a cavity in the housing covered by a lid.

4. A syringe according to claim 2, wherein the compartment is an inner space in a cap mounted on the housing.

5. A syringe according to claim 2, wherein the housing includes a slide-in drawer which forms the compartment.

6. A syringe according to claim 4, wherein said cap has a surface which presses against the skin of the user when a needle mounted on said housing is injected into a patient.

7. A syringe according to claim 1, wherein the compartment is provided in a location spaced from the needle receiving member.

8. A syringe according to claim 1, wherein said housing is box-shaped, wherein said housing has a central axis parallel to a needle when mounted on said housing, and wherein said needle receiving member and compartment are on opposite sides of said central axis.

* * * * *